(12) United States Patent
Brown et al.

(10) Patent No.: US 6,753,335 B2
(45) Date of Patent: Jun. 22, 2004

(54) QUINOLINYL-PIPERIDIN-4-YLIDENE-METHYL-BENZAMIDE DERIVATIVES FOR THE TREATMENT OF PAIN

(75) Inventors: William Brown, Blainville (CA); Christopher Walpole, Hudson (CA); Zhongyong Wei, Pierrefonds (CA)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/240,114

(22) PCT Filed: Mar. 30, 2001

(86) PCT No.: PCT/SE01/00708
§ 371 (c)(1),
(2), (4) Date: Jan. 21, 2003

(87) PCT Pub. No.: WO01/74806
PCT Pub. Date: Oct. 11, 2001

(65) Prior Publication Data
US 2003/0199548 A1 Oct. 23, 2003

(30) Foreign Application Priority Data
Apr. 4, 2000 (SE) .............................................. 0001208

(51) Int. Cl.$^7$ .......................... A61K 31/47; C07D 9/28; C07D 215/16; C07D 211/06; C07D 211/26
(52) U.S. Cl. .......................... 514/314; 546/22; 546/152; 546/197; 546/205; 546/213; 546/229; 546/232; 546/234
(58) Field of Search ............................ 514/314; 546/22, 546/152, 197, 205, 213, 229, 232, 234

(56) References Cited

U.S. PATENT DOCUMENTS

| | | | |
|---|---|---|---|
| 2,898,339 A | 8/1959 | Wheeler et al. | 260/293.4 |
| 4,581,171 A | 4/1986 | Kennis et al. | 260/243.3 |
| 4,816,586 A | 3/1989 | Portoghese | 544/340 |
| 4,939,137 A | 7/1990 | Russell et al. | 514/183 |
| 5,140,029 A | 8/1992 | Kennis et al. | 514/272 |
| 5,574,159 A | 11/1996 | Chang et al. | 544/396 |
| 5,683,998 A | 11/1997 | Shibayama et al. | 514/218 |
| 6,187,792 B1 * | 2/2001 | Delorme et al. | 514/320 |
| 6,455,545 B2 | 9/2002 | Delorme et al. | 514/320 |

FOREIGN PATENT DOCUMENTS

| | | | | |
|---|---|---|---|---|
| WO | WO 93/15062 | 8/1993 | ......... | C07D/241/04 |
| WO | WO 97/23466 | 7/1997 | ......... | C07D/241/04 |
| WO | WO 98/28275 | * 7/1998 | | |
| WO | WO 99/33806 | 7/1999 | ......... | C07D/211/58 |

OTHER PUBLICATIONS

Barber, et al., "Antinociceptive Effects of the 5–HT$_2$ Antagonist Ritanserin in Rats: Evidence for an Activation of Descending Monoaminergic Pathways in the Spinal Cord," *Neuroscience Letters* 99:234–238 (1989).

Bilsky, et al., "SNC 80, a Selective, Nonpeptidic and Systemically Active Opioid *Delta* Agonist," *J. Pharmacol. Experi. Ther.* 273:359–366 (1995).

Greene, "Protective Groups in Organic Synthesis," Wiley & Sons, pp. 218, 220, 232, 233, 251 (1982).

Takemori, et al., "Selective Natrexone–Derived Opioid Receptor Antagonists," *Annu. Rev. Pharmacol. Toxicol.* 32:239–269 (1992).

Wei, et al., "*N,N*–Diethyl–4–(phenylpiperidin–4–ylidenemethyl) benzamide: A Novel, Exceptionally Selective, Potent δ Opioid Receptor Agonist with Oral Bioavailability and Its Analogues," *J. Med. Chem.* 43:3895–3905 (2000).

Zhang, et al., "Probes for Narcotic Receptor Mediated Phenomena. 26.$^{1-3}$ Synthesis and Biological Evaluation of Diarylmethylpiperazines and Diarylmethylpiperidines as Novel, Nonpeptide δ Opioid Receptor Ligands," *J. Med. Chem.* 42:5455–5463 (1999).

* cited by examiner

*Primary Examiner*—D. Margaret Seaman
(74) *Attorney, Agent, or Firm*—Michael A. Sanzo; Fitch, Even, Tabin & Flannery

(57) ABSTRACT

Compounds of general formula I

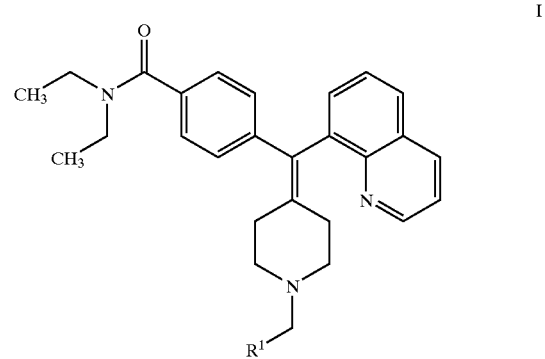

R$^1$ is selected from any one of phenyl, pyridinyl, thienyl, furanyl, imidazolyl, and triazolyl;

where each R$^1$ phenyl ring and R$^1$ heteroaromatic ring may optionally and independently be further substituted by 1, 2 or 3 substituents selected from straight and branched C$_1$–C$_6$ alkyl, NO$_2$, CF$_3$, C$_1$–C$_6$ alkoxy, chloro, fluoro, bromo, and iodo. The substitutions on the phenyl ring and on the heteroaromatic ring may take place in any position on said ring systems;

are disclosed and claimed in the present application, as well as their pharmaceutically acceptable salts and pharmaceutical compositions comprising the novel compounds and their use in therapy, in particular in the management of pain.

11 Claims, No Drawings

QUINOLINYL-PIPERIDIN-4-YLIDENE-METHYL-BENZAMIDE DERIVATIVES FOR THE TREATMENT OF PAIN

CROSS REFERENCE TO RELATED APPLICATIONS

The present application represents U.S. national stage of international application No. PCT/SE01/00708, which had an international filing date of Mar. 30, 2001, and which was published in English under PCT Article 21 (2) on Oct. 11, 2001. The international application claims priority to Swedish application 0001208-8 on Apr. 4, 2000.

FIELD OF THE INVENTION

The present invention is directed to novel compounds, to a process for their preparation, their use and pharmaceutical compositions comprising the novel compounds. The novel compounds are useful in therapy, and in particular for the treatment of pain.

BACKGROUND AND PRIOR ART

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immunomodulatory activities.

The identification of at least three different populations of opioid receptors (μ, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. One example of a non-peptidic δ-agonist is SNC80 (Bilsky E. J el al., *Journal of Pharmacology and Experimental Therapeutics*, 273(1), pp. 359–366 (1995)). There is however still a need for selective δ-agonists having not only improved selectivity, but also an improved side-effect profile.

Thus, the problem underlying the present invention was to find new analgesics having improved analgesic effects, but also with an improved side-effect profile over current μ agonists, as well as having improved systemic efficacy.

Analgesics that have been identified and are existing in the prior art have many disadvantages in that they suffer from poor pharmacokinetics and are not analgesic when administered by systemic routes. Also, it has been documented that preferred δ agonist compounds, described within the prior art, show significant convulsive effects when administered systemically.

We have now found that certain compounds not specifically disclosed by, but included within the scope of WO 98/28275, exhibit surprisingly improved δ-agonist properties and in vivo potency.

OUTLINE OF THE INVENTION

The novel compounds according to the present invention are defined by the formula I

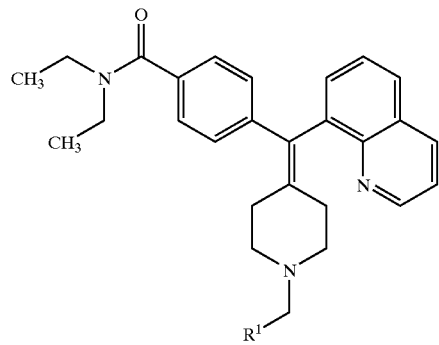

wherein
R$^1$ is selected from any one of

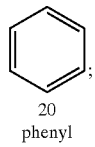

phenyl (i)

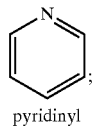

pyridinyl (ii)

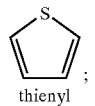

thienyl (iii)

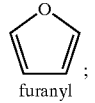

furanyl (iv)

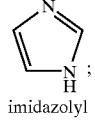

imidazolyl (v)

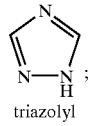

triazolyl (vi)

where each R$^1$ phenyl ring and R$^1$ heteroaromatic ring may optionally and independently be further substituted by 1, 2 or 3 substituents selected from straight and branched $C_1$–$C_6$ alkyl, $NO_2$, $CF_3$, $C_1$–$C_6$ alkoxy, chloro, fluoro, bromo, and iodo. The substitutions on the phenyl ring and on the heteroaromatic ring may take place in any position on said ring systems;

A preferred embodiment of the present invention is a compound according to FIG. I wherein R$^1$ is as defined above and each R$^1$ phenyl ring and R$^1$ heteroaromatic ring may independently be further substituted by a methyl group.

A more preferred embodiment of the present invention is a compound according to FIG. I wherein R$^1$ is pyridinyl, thienyl or furanyl.

Within the scope of the invention are also salts and enantiomers of the compounds of the formula I, including enantiomers of salts.

When the phenyl ring and the heteroaromatic ring(s) are substituted, the preferred substituents are selected from anyone of $CF_3$, methyl, iodo, bromo, fluoro and chloro.

Reaction step g in Scheme 1, vide infra, is performed by reacting an intermediate compound of the general formula II

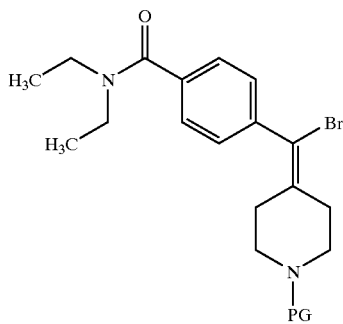

wherein PG is a urethane or benzyl-like protecting group, such as Boc, with 8-quinolinyl boronic acid, using a palladium catalyst, e.g. $Pd(PPh_3)_4$, in the presence of a base, e.g. $Na_2CO_3$, to give the compounds of general formula III,

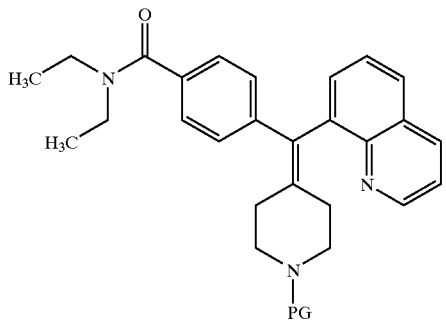

which is thereafter deprotected, under standard conditions and alkylated under reductive conditions with a compound of the general formula $R^1$—CHO to give compounds of the general formula I.

Suitable palladium catalysts include, but is not limited to, $PdCl_2$(with a phosphine), $Pd(OAc)_2$ (with a phosphine), $Pd(dba)_2$, $PdCl_2(dppf) \cdot CH_2Cl_2$, $Pd(PPh_3)_4$, and Pd/C.

Suitable bases include, but is not limited to, triethylamine, sodium and potassium carbonate.

Suitable reducing agents to be used includes, but is not limited to, sodium cyanoborohydride and sodium triacetoxyborohydride.

The novel compounds of the present invention are useful in therapy, especially for the treatment of various pain conditions such as chronic pain, neuropathic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, anxiety, urinary incontinence, various mental illnesses, cough, lung oedema, various gastrointestinal disorders, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

Also within the scope of the invention is the use of any of the compounds according to the formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment.

A further aspect of the present invention is intermediates of the general formula II,

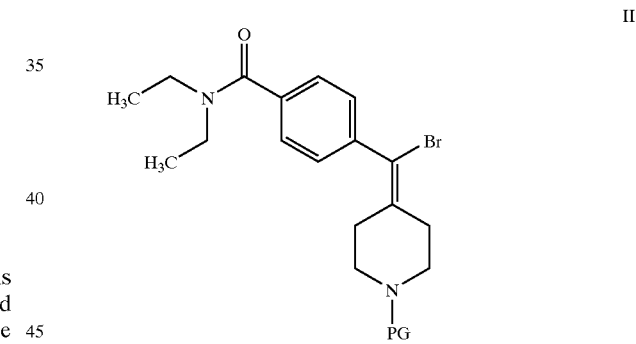

wherein PG is a urethane or benzyl-like protecting group, such as Boc,

Methods of Preparation

The compounds according to the present invention may be prepared by following the known procedures described in e.g. "*Advanced Organic Chemistry*" third edition by Jerry March, John Wiley and Sons Inc.; New York (1985): Step (a): p848; Step (b): p848; Step (c): p657; Step (d):p875; Step (e): p371–373; Step (f): p364–366; Step (g): N. Miyaura and A. Suzuki, *Chem. Rev.*, 95, 2457–2483(1995); Step (h): "*Protective Groups in Organic synthesis*" p 327–329, by Theodora W. Greene and Peter G. M. Wuts, Second Edition, John Wiley and Sons Inc.; New York (1991). These references are hereby incorporated in full.

EXAMPLES

The invention will now be described in more detail by the following Examples, which are not to be construed as limiting the invention.

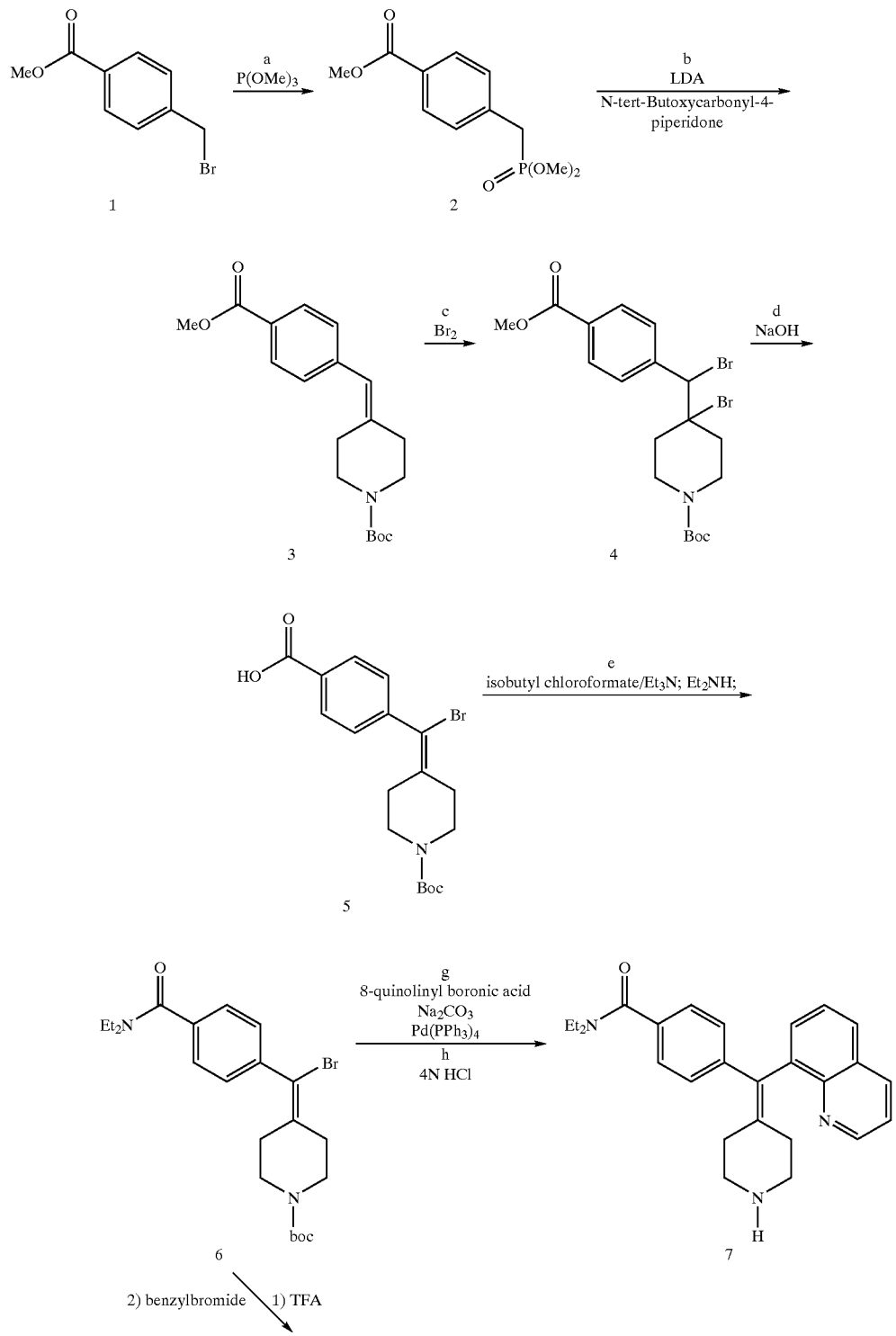

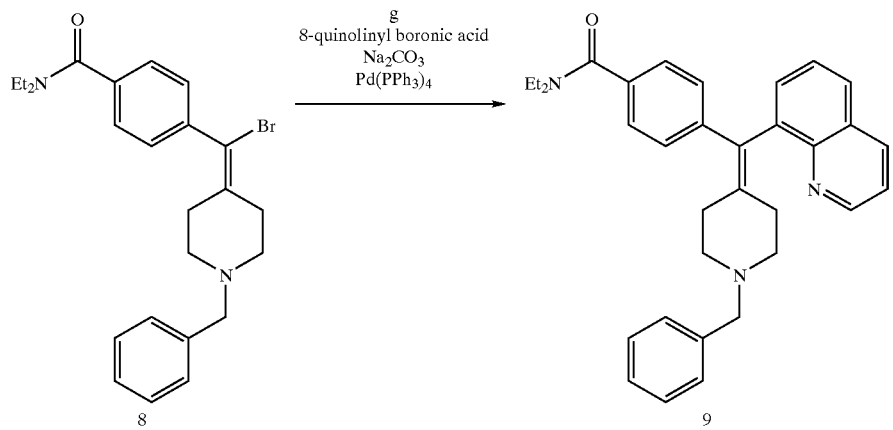

Example 1

Preparation of N,N-diethyl-4-(8-guinolinyl-piperidin-4-ylidene-methyl)-benzamide (compound 7)

(i) Preparation of 4-(4-methoxycarbonyl-benzylidene)-piperidine-1-carboxylic acid tert-butyl ester (compound 3)

A mixture of compound 1 (11.2 g, 49 mmol) and trimethyl phosphite (25 mL) was refluxed under $N_2$ for 5 hrs. Excess trimethyl phosphite was removed by co-distillation with toluene to give compound 2 in quantitative yield: $^1$H NMR (CDCl$_3$) δ3.20 (d, 2H, J=22 Hz), 3.68 (d, 3H 10.8 Hz), 3.78 (d, 3H, 11.2 Hz), 3.91 (s, 3H), 7.38 (m 2H), 8.00 (d, 2H, J=8 Hz).

(ii) To a solution of the above product (compound 2) in dry THF (200 mL) was added dropwise lithium diisopropylamide (32.7 mL 1.5 M in hexanes, 49 mmol) at −78° C. The reaction mixture was then allowed to warm to room temperature prior to addition of N-tert-butoxycarbonyl-4-piperidone (9.76 g, 49 mmol in 100 mL dry THF). After 12 hrs, the reaction mixture was quenched with water (300 mL) and extracted with ethyl acetate (3×300 mL). The combined organic phases were dried over MgSO$_4$ and evaporated to give a crude product, which was purified by flash chromatography to provide compound 3 as a white solid (5.64 g, 35%):

IR (NaCl) 3424, 2974, 2855, 1718, 1688, 1606, 1427, 1362, 1276 cm$^{-1}$;

$^1$H NMR (CDCl$_3$) δ1.44 (s, 1H), 2.31 (t, J=5.5 Hz, 2H), 2.42 (t, J=5.5 Hz, 2H), 3.37 (t, J=5.5 Hz, 2H), 3.48 (t, J=5.5 Hz, 2H), 3.87(s, 3H), 6.33 (s, 1H), 7.20 (d J=6.7 Hz, 2H), 7.94 (d, J=6.7 Hz, 2H); $^{13}$C NMR (CDCl$_3$) δ28.3, 29.2, 36.19, 51.9, 123.7, 127.8, 128.7, 129.4, 140.5, 142.1, 154.6, 166.8.

(iii) Preparation of 4-bromo-4[bromo-(4-methoxycarbonyl-phenyl)-methyl]-piperidine-1-carboxylic acid tert-butyl ester (compound 4)

To a mixture of compound 3 (5.2 g, 16 mmol) and K$_2$CO$_3$ (1.0 g) in dry dichloromethane (200 mL) was added a solution of bromine (2.9 g, 18 mmol) in 30 mL CH$_2$Cl$_2$ at 0° C. after 1.5 hrs at room temperature, the solution after filtration of K$_2$CO$_3$ was condensed. The residue was then dissolved in ethyl acetate (200 mL), washed with water (200 mL), 0.5 M HCl (200 mL) and brine (200 mL), and dried over MgSO$_4$. Removal of solvents provided a crude product, which was recrystallized from methanol to give compound 4 as a white solid (6.07 g, 78%): IR (NaCl) 3425, 2969, 1725, 1669, 1426, 1365, 1279, 1243 cm$^{-1}$ ;

$^1$H NMR (CDCl$_3$) δ1.28 (s, 9H), 1.75 (m, 2H), 1.90 (m, 2H), 2.1 (m, 4H), 3.08 (br, 4H), 3.90 (s,3H), 4.08 (br, 4H), 5.14 (s,1H), 7.57 (d, J=8.4 Hz, 2H) 7.98 (d, J=8.4 Hz, 2H); 7.98 (d, J=8.4 Hz, 2H);

$^{13}$C NMR (CDCl$_3$) δ28.3, 36.6, 38.3, 40.3, 52.1 63.2, 72.9, 129.0, 130.3, 130.4, 141.9, 154.4, 166.3.

(iv) Preparation of 4-[bromo-(4-caboxy-phenyl)-methylene]-piperidine-1-carboxylic acid tert-butyl ester (compound 5)

A solution of compound 4 (5.4 g 11 mmol) in methanol (300 mL) and 2.0 M NaOH (100 mL) was heated at 40° C. for 3 hrs. The solid was collected by filtration, and dried overnight under vacuum. The dry salt was dissolved in 40% acetonitrile/water, and was adjusted to pH 2 using concentrated HCl. The desired product compound 5 (3.8 g, 87%) was isolated as a white powder by filtration: $^1$H NMR (CDCl$_3$) δ1.45 (s, 9H), 2.22 (dd, J=5.5 Hz, 6.1 Hz, 2H), 2.64 (dd, J=5.5 Hz, 6.1 Hz, 2H), 3.34 (dd, J=5.5 Hz, 6.1 Hz, 2H), 3.54 (dd, J=5.5 Hz, 6.1 Hz, 2H), 7.35 (d, J=6.7 Hz, 2H), 8.08 (d, J=6.7 Hz, 2H); $^{13}$C NMR (CDCl$_3$) δ28.3, 31.5, 34.2, 44.0, 115.3, 128.7, 129.4 130.3, 137.7, 145.2, 154.6, 170.3.

(v) Preparation of 4-[bromo-(4-diethylcarbamoyl-phenyl)-methylene]-piperidine-1-carboxylic acid tert-butyl ester (compound 6)

To a solution of compound 5 (1.0 g, 2.5 mmol) in dry dichloromethane (10 mL) at −20° C. was added isobutylchloroformate (450 mg, 3.3 mmol). After 20 min at −20° C. diethylamine (4 mL) was added and the reaction was allowed to warm to room temperature. After 1.5 hrs the solvents were evaporated and the residue was partitioned between ethyl acetate and water. The organic phase was washed with brine and dried over MgSO$_4$. Removal of solvents provided a crude product, which was purified by flash chromatography to give compound 6 as white needles (800 mg, 73%): IR (NaCl) 3051, 2975, 1694, 1633, 1416, 1281, 1168, 1115 cm$^{-1}$; $^1$H NMR (CDCl$_3$) δ1.13 (br, 3H), 1.22 (br, 3H), 1.44 (s, 9H),2.22 (t, J=5.5 Hz, 2H), 2.62 (t, J=5.5 Hz, 2H), 3.33 (m, 4H), 3.55 (m, 2H), 7.31 (d, J=8.0 Hz, 2H), 7.36 (d, J=8.0 Hz, 2H); $^{13}$C NMR (CDCl$_3$) δ12.71, 14.13, 28.3, 31.5, 34.2, 39.1, 43.2, 79.7, 115.9, 126.3, 129.3, 136.8, 137.1, 140.6, 154.6, 170.

(vi) Preparation of N,N-diethyl-4-(8-quinolinyl-piperidin-4-ylidene-methyl)-benzamide (compound 7).

A mixture of compound 6 (902 mg, 2.0 mmol), 8-quinolinyl boronic acid (860 mg, 5.0 mmol), 2M Na$_2$CO$_3$ (2.5 mL), and tetrakis(triphenyl phosphine) palladium(0) (20 mg) in toluene (degassed, 5 mL) and ethanol (degassed. 5 mL) was refluxed at 90° C. for 4 hrs under N$_2$. The reaction mixture was then cooled down to r.t., and extracted with ethyl acetate (2×100 mL). The combined organic phases were dried over MgSO$_4$ and evaporated to give a crude product.

The above product was treated with 4.0 M HCl in dioxane at 50° C. for 2 h. After evaporation, the residue was dissolved in 1 M HCl (100 mL) and impurities were extracted with diethyl ether (3×100 mL). The aqueous phase was basified with NH$_4$OH and extracted with dichloromethane (3×100 mL). The combined organic phases were washed with brine, dried over MgSO$_4$ and evaporated to give the title compound 7 (729 mg, 91 %).

$^1$H—NMR (400 MHz, CDCl$_3$) δ1.07 (3 H, br m, C H$_3$CH$_2$—), 1.20 (3 H, br m, C H$_3$CH$_2$—), 200 (2 H, m, piperidine CH—), 2.46 (1H, s, NH), 2.52 (2H, m, piperidine CH—), 2.75 (1H, m,piperidine CH—), 2.92 (2H, m, piperidine CH—),3.05 (1 H, m, piperidine CH—) 3.22 (2 H, m, C H$_2$N—), 3.49 (2 H, m, CH$_2$N—), 7.23 (2 H, m, ArH), 7.32 (2H, m, Ar H ), 7.36 (1 H, m, ArH), 7.49 (2 H, m, ArH), 7.72 (1 H, dd, J=6.4, 3.2 Hz, ArH), 8.11 (1 H, dd, J=8.4, 1.6 Hz, ArH), 8.91 ((1 H, dd, J=4.0, 1.6 Hz, ArH);Its HCl salt: m.p. >170° C. (Dec.); IR (NaCl) 3410, 2973, 1614, 1551, 1436, 1284 cm$^{-1}$.

Example 2

Preparation of N,N-diethyl-4-(8-quinolinyl-N-benzyl-piperidin-4-ylidene-methyl)-benzamide (compound 9)

(i) Preparation of N,N-diethyl-4-(bromo-N-benzyl-piperidine-4-ylidene-methyl)-benzamide (compound 8)

Compound 6 prepared in Example 1(v) above (2.26 g, 5.0 mmol), was treated with TFA (25 mL) in dichloromethane (25 mL) at room temperature. After 2 h, the reaction mixture was condensed to give a residue, which was dissolved in acetonitrile (20 mL), and was reacted with benzyl bromide (5.0 mmol) at r.t. for 2 h. The reaction mixture was condensed, and then dissolved in ethyl acetate (100 mL). The organic solution were washed with 1N NH$_4$OH and brine, dried over MgSO$_4$. Removal of solvents provided a crude product, which was purified by flash chromatography to give compound 8 as an oil (1.0 g, 45%): IR (NaCl) 2971, 1630, 1427, 1287, 1094 cm$^{-1}$ ; $^1$H NMR (CDCl$_3$) δ1.13 (br, 3H), 1.23 (br, 3H), 2.28 (m, 2H), 2.37 (m, 2H), 2.55 (m, 2H), 2.69 (m, 2H), 3.27 (m, 2H), 3.53 (br,4H), 7.31 (m, 4H).

(ii) Preparation of N,N-diethyl-4-(8-quinolinyl-N-benzyl-piperidin-4-ylidene-methyl)-benzamide (compound 9)

A mixture of compound 8 prepared in step (i) above (1.32 mg, 3.0 mmol), 8-quinolinylboronic acid (1.04 mg, 6.0 mmol), 2M Na$_2$CO$_3$ (3.0 mL), and tetrakis(triphenyl phosphine) palladium(0) (20 mg) in toluene (degassed, 5 mL) and ethanol (degassed, 5 mL) was refluxed at 90° C. for 2 hrs under N$_2$. The reaction mixture was then cooled down to r.t., and extracted with ethyl acetate (2×100 mL). The combined organic phases were washed with brine, dried over MgSO$_4$. Removal of solvents provided a crude product, which was purified-by flash chromatography to give the desired title compound 9 (832 mg, 57%):IR (NaCl) 2971, 1625, 1551,1426, 1287cm$^{-1}$; $^1$H-NMR (400 MHz, CDCl$_3$) δ1.04 (3 H, br m, CH$_3$CH$_2$—), 1.17 (3 H, br, m, C H$_3$CH$_2$—),2.03 (2 H, m, piperidine CH—), 2.30 (1H, m, piperidine CH), 2.51 (2H, m, piperidine CH), 2.59 (2 H, m, piperidine CH—), 2.68 (1 H, m, piperidine CH—), 3.19 (2 H, m, CH$_2$N—), 3.49 (2 H, m, CH$_2$N—), 3.52 (2H, s, PhC H$_2$N), 7.35(10 H, m, ArH), 7.46 (2 H, m, ArH), 7.71 (1 H, m, ArH), 8.10 (1 H, m, ArH), 8.09 (1 H, m, ArH).

Examples 3–10

Compounds 10–17 of Examples 3–10, were prepared by following the synthetic procedures on of Scheme 2 below.

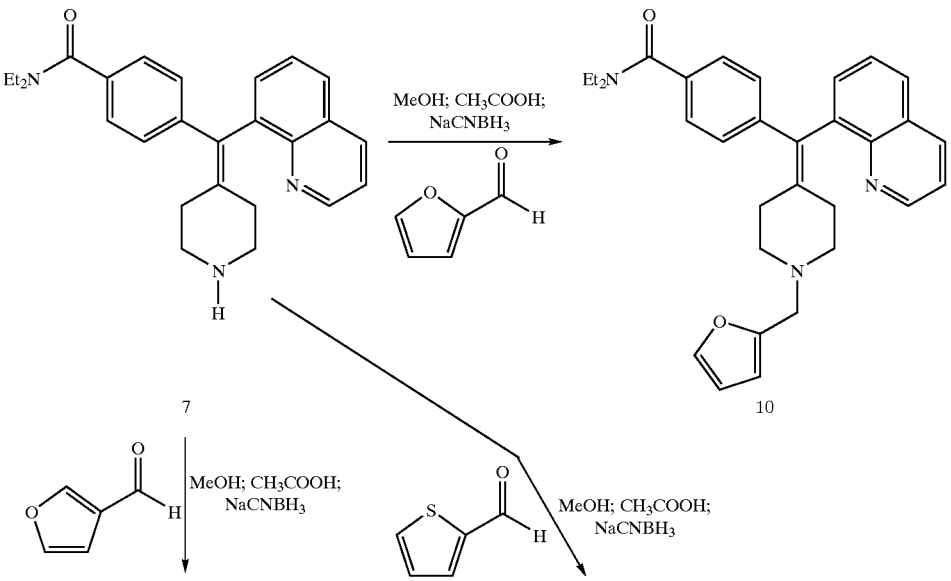

Scheme 2: 1(3)

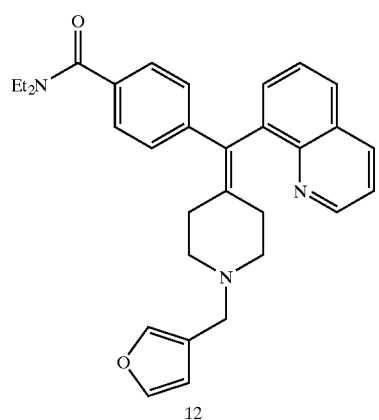
12
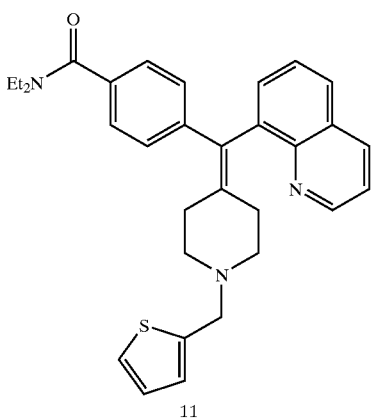
11
Scheme 2: 2(3)
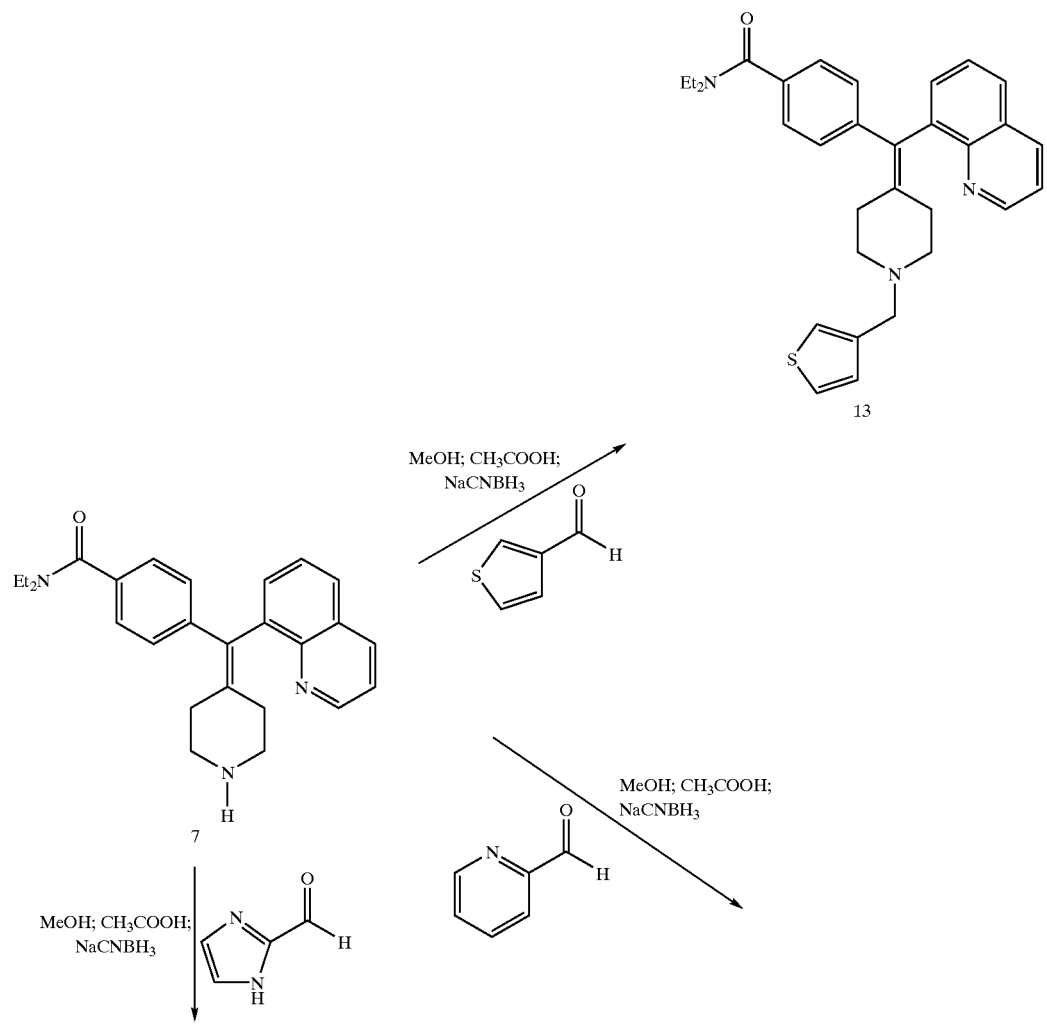

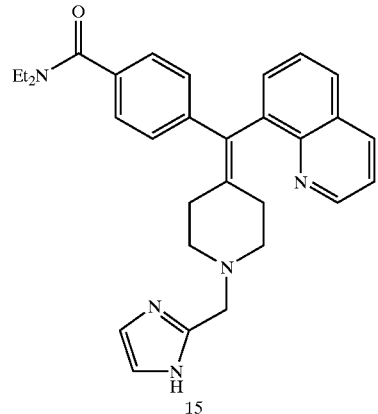
15
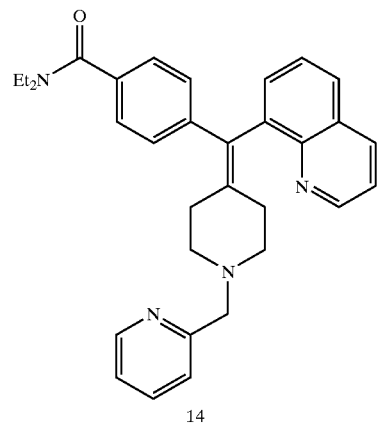
14
Scheme 2: 3(3)
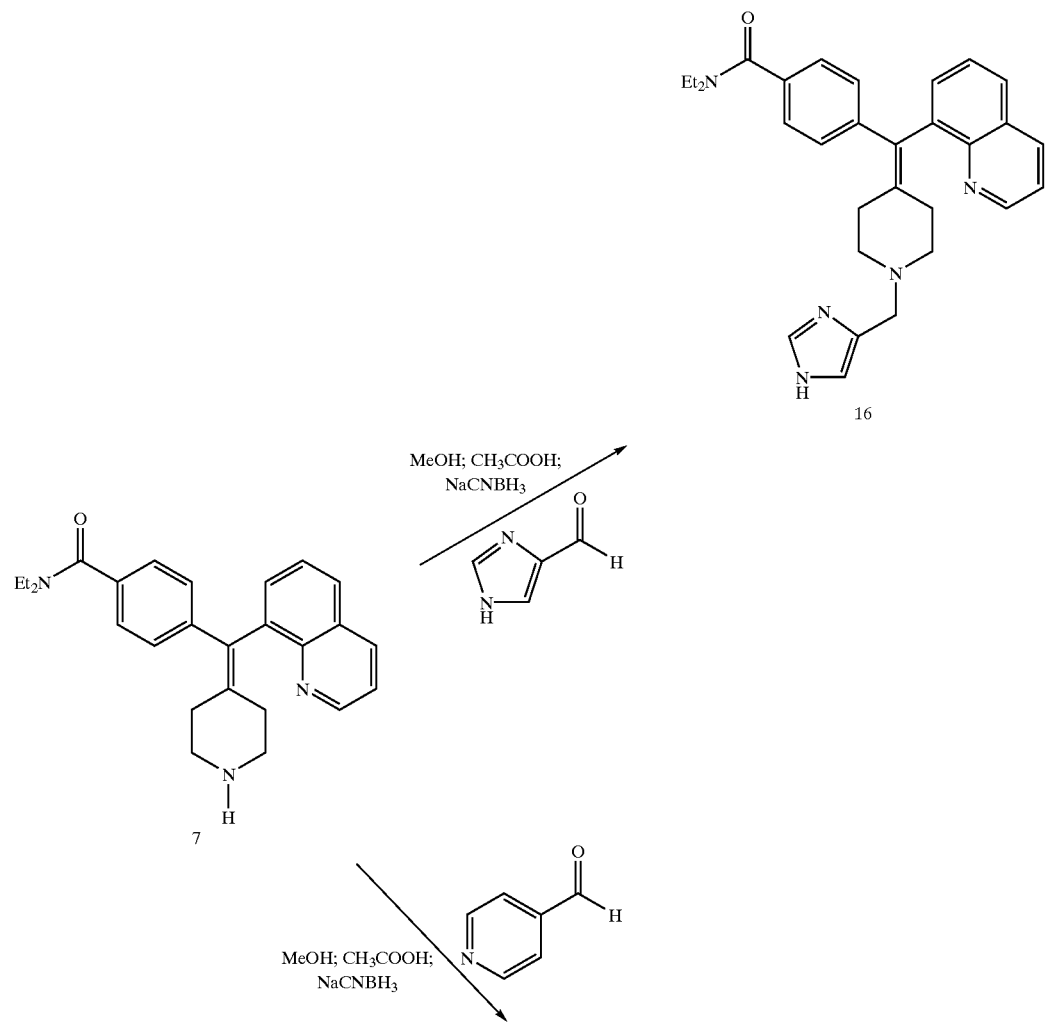

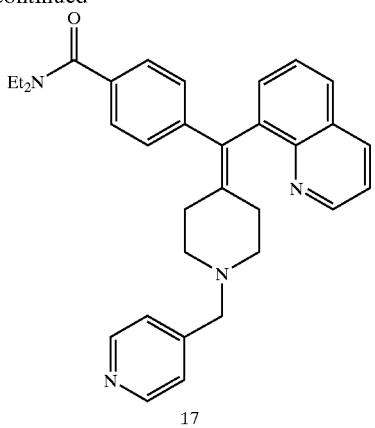

17

Example 3

Preparation of N,N-diethyl-4-[[1-(2-furylmethyl)-4-piperidinylidene](8-quinoline)methyl]benzamide (compound 10)

To a room temperature solution of secondary amine (300 mg; 0.75 mmol) in methanol (8 ml) was added 2-furaldehyde (261 μ; 3.15 mmol), followed by acetic acid (0.5 ml). The mixture was stirred for two hours then sodium cyanoborohydride (198 mg; 3.15 mmol) was added. The reaction mixture was stirred overnight, then sodium hydroxide 2N was added and the mixture extracted with methylene chloride. Combined methylene chloride extracts were dried over anhydrous sodium sulphate, filtered and concentrated under reduced pressure. Reverse phase purification.

(M+1) calculated: 480.62, (M+1) observed: 480.16

Anal.: calculated for ($C_{31}H_{33}N_3O_2$ X 2.20 $C_2HO_2F_3$ X 1.00 $H_2O$): C: 56.81%; H: 5.01%; N:5.61%; found: C:56.84%; H:4.96%: N:5.59%

[1] HNMR ($CD_3OD$): 8.86–8.90 (m, 1H), 8.38–8.50 (m, 1H), 7.68–7.96 (m, 1H) 7.48–7.66 (M, 4H), 7.31 (d, 2H, J=7.6 Hz), 7.21 (d, 2H, J=7.6 Hz), 6.61–6.62 (m, 1H), 6.43–6.44 (m, 1H), 4.34 (s, 2H), 2.04–3.62 (m, 12H), 1.07–1.16 (m, 3H), 0.94–1.03 (m, 3H)

Example 4

Preparation of N,N-diethyl-4-{8-quinolinyl[1-(2-thienylmethyl)-4-piperidinylidene]methyl}benzamide (compound 11)

To a room temperature solution of secondary amine (300 mg; 0.75 mmol) in methanol (8 ml) was added thiophene-2-carboxaldehyde (294.4 μl; 3.15 mmol), followed by acetic acid (0.5 ml). The mixture was stirred for two hours then sodium cyanoborohydride (198 mg; 3.15 mmol) was added. The reaction mixture was stirred overnight, then sodium hydroxide 2N was added and the mixture extracted with methylene chloride. Combined methylene chloride extracts were dried over anhydrous sodium sulphate, filtered and concentrated under reduced pressure. Reverse phase purification.

(M+1) calculated: 496.69, (M+1) observed: 496.09

Anal.: calculated for ($C_{31}H_{33}N_3OS$ X 2.50$C_2HO_2F_3$X 0.60 $H_2O$): C: 54.63%; H:4.67%; N:5.31%; found: C:54.62%; H:4.64%; N:5.45%

$^1$HNMR ($CD_3$ OD): 8.89–8.90 (m, 1H), 8.42–8.56 (m, 1H), 7.86–7.98 (m, 1H), 7.53 (d, 1H, J=5.2 Hz), 7.50–7.70 (m, 3H), 7.30 (d, 2H, J=7.6 Hz), 7.20–7.24 (m, 1H), 7.20 (d, 2H, J=8.0 Hz), 7.02–7.06 (m, 1H), 4.50 (s, 2H), 2.04–3.66 (m, 12H), 1.06–1.16 (m, 3H), 0.94 1.02 (m, 3H)

Example 5

Preparation of N,N-diethyl-4-[[1-(3-furylmethyl)-4-piperidinylidene](8-quinolinyl)methyl]benzamide (compound 12)

To a room temperature solution of secondary amine (300 mg; 0.75 mmol) in methanol (8 ml) was added 3-furaldehyde (272.4 μl; 3.15 mmol), followed by acetic acid (0.5 ml). The mixture was stirred for two hours then sodium cyanoborohydride (198 mg; 3.15 mmol) was added. The reaction mixture was stirred overnight, then sodium hydroxide 2N was added and the mixture extracted with methylene chloride. Combined methylene chloride extracts were dried over anhydrous sodium sulphate, filtered and concentrated under reduced pressure. Reverse phase purification.

(M+1) calculated: 480.62, (M+1) observed: 480.33

Anal.: calculated for ($C_{31}H_{33}N_3O_2$X 1.80 $C_2HO2F_3$ X 0.80 $H_2O$): C:59.43%; H:5.25% N:6.01%; found: C:59.38%; H:5.24%; N:5.98%

$^1$HNMR ($CD_3OD$): 8.80–8.88 (m, 1H), 8.30–8.42 (m, 1H), 7.80–7.92 (m, 1H), 7.44–7.68 (m, 4H), 7.26–7.36 (m, 2H), 7.16–7.24 (m, 3) 6.50 (s, 2H), 2.86–3.62 (m, 9H), 2.48–2.66 (m, 1H), 2.06–2.36 (m, 2H), 1.06–1.16 (m, 3H), 0.94–1.04 (m, 3H)

Example 6

Preparation of N,N-diethyl-4-{8-quinolinyl[1-(3-thienylmethyl)-4-piperidinylidene]methyl}benzamide (compound 13)

To a room temperature solution of secondary amine (300 mg; 0.75 mmol) in methanol (8 ml) was added thiophene-3-carboxaldehyde (276 μl: 3.15 mmol), followed by acetic acid (0.5 ml). The mixture was stirred for two hours then sodium cyanoborohydride (198 mg: 3.15 mmol) was added. The reaction mixture was stirred overnight, then sodium hydroxide 2N was added and the mixture extracted with methylene chloride. Combined methylene chloride extracts were dried over anhydrous sodium sulphate, filtered and concentrated under reduced pressure. Reverse phase purification.

(M+1) calculated: 496.69, (M+1) observed: 496.11

Anal.: calculated for ($C_{31}H_{33}N_3OS$ X 2.70 $C_2HO_2F_3$ X 0.70$H_2O$): C:53.57%; H:4.58%; N:5.15%; found: C:53.56%; H:4.54%; N:5.40%

$^1$HNMR (CD$_3$OD): 8.82–8.90 (m, 1H), 8.34–8.50 (m, 1H), 7.82–7.96 (m, 1H), 7.42–7.70 (m, 4H), 7.24–7.36 (m, 2H), 7.20 (d, 2H, J=7.2 Hz), 7.08–7.14 (m,2H), 4.28 (s, 2H), 2.04–3.58 (m, 12H), 1.06–1.16 (m, 3H), 0.92–1.03 (m, 3H)

Example 7

Preparation of N,N-diethyl-4-[[(1-(2-pyridinylmethyl)-4-piperidinylidene](8-quinolinyl) methyl]benzamide (compound 14)

To a room temperature solution of secondary amine (300 mg; 0.75 mmol) in methanol (8 ml) was added 2-pyridinecarboxaldehyde (299.6 µl; 3.15 mmol), followed by acetic acid (0.5 ml). The mixture was stirred for two hours then sodium cyanoborohydride (198 mg; 3.15 mmol) was added. The reaction mixture was stirred overnight, then sodium hydroxide 2N was added and the mixture extracted with methylene chloride. Combined methylene chloride extracts were dried over anhydrous sodium sulphate, filtered and concentrated under reduced pressure. Reverse phase purification.

(M+1) calculated: 491.65, (M+1) observed: 491.11

Anal.,: calculated for ($C_{32}H_{34}N_4O$ X 2.40 $C_2HO_2F_3$ X 1.00 $H_2O$): C:56.50%; H:4.95%; N:7.16%; found: C:56.47%; H:4.97%; N:7.27%

$^1$HNMR (CD$_3$OD): 8.91 (dd, 1H, J=4.4, 1.2 Hz), 8.57 (d, 1H, J=4.4 Hz), 8.47 (dd, 1H, J=8.0, 1.6 Hz), 7.91 (dd, 1H, J=7.2, 2.8 Hz), 7.79 (dt, 1H, J=8.0, 1.6 Hz), 7.56–7.62 (m, 3H), 7.39 (d, 1H, J=7.2 Hz), 7.32 (d, 2H, J=8.0 Hz), 7.30–7.36 (m, 1H), 7.21 d, 2H, J=8.4 Hz), 4.41 (s, 2H), 3.08–3.56 (m, 8H), 2.72–2.88 (m, 2H), 2.18–2.36 (m, 2H), 1.06–1.16 (m, 3H), 0.92–1.02 (m, 3H)

Example 8

Preparation of N,N-diethyl-4-[[(1H-imidazol-2-ylmethyl)-2-ylmethyl)-4-piperidinylidene] (8quinolinyl)methyl]benzamide (compound 15)

To a room temperature solution of secondary amine (300 mg; 0.75 mmol) in methanol (8 ml) was added 2-imidazolecarboxaldehyde (302.7 mg; 3.15 mmol), followed by acetic acid (0.5 ml). The mixture was stirred for two hours then sodium cyanoborohydride (198 mg; 3.15 mmol) was added. The reaction mixture was stirred overnight; then sodium hydroxide 2N was added and the mixture extracted with methylene chloride. Combined methylene chloride extracts were dried over anhydrous sodium sulphate, filtered and concentrated under reduced pressure. Reverse phase purification.

(M+1) calculated: 480.63, (M+1) observed: 479.97

Anal.: calculated for ($C_{30}H_{33}N_5O$ X 2.80 $C_2HO_2F_3$ X 2.20 $H_2O$): C:50.99%: H:4.83%; N:8.35%; found: C:51.07%; H:4.90%; N:8.10%

$^1$HNMR (CD$_3$OD): 8.91 (dd, 1H, J=4.4, 1.2 Hz), 8.60 (d, 1H, J=7.6 Hz), 7.96 (dd, 1H, J=6.4, 3.6 Hz ),7.62–7.68 (m, 3H), 7.39 (s, 2H),7.30 (d, 2H, J=8.0 Hz), 7.19 (d, 2H, J=8.8 Hz), 4.09 (s, 2H), 3.34–3.46 (m, 2H), 3.02–3.22 (m, 4H), 2.78–2.88 (m, 2H), 2.60–2.70 (m, 2H), 2.04–2.18 (m, 2H), 1.06–1.16 (m, 3H), 0.92–1.02 (m, 3H)

Example 9

Preparation or N,N-diethyl-4-[[(1-(1H-imidazol-4-ylmethyl)-4-piperidinylidene](8-quinolinyl) methyl] benzamide (compound 16)

To a room temperature solution of secondary amine (300 mg; 0.75 mmol) in methanol (8 ml) was added 4(5)-imidazolecarboxaldehyde (302.7 mg; 3.15 mmol), followed by acetic acid (0.5 ml). The mixture was stirred for two hours then sodium cyanoborohydride (198 mg; 3.15 mmol) was added. The reaction mixture was stirred overnight, then sodium hydroxide 2N was added and the mixture extracted with methylene chloride. Combined methylene chloride extracts were dried over anhydrous sodium sulphate, filtered and concentrated under reduced pressure. Reverse phase purification.

(M+1) calculated: 480.63, (M+1) observed: 480.15

Anal.: calculated for ($C_{30}H_{33}N_5O$ X3.70 $C_2HO_2F_3$ X1.20 $H_2O$): C:48.66%; H:4.27%; N:7.59%; found: C:48.68%; H:4.33%; N:7.49%

$^1$HNMR (CD$_3$OD): 8.90 (dd, 1H. J=4.4, 1.2 Hz), 8.71–8.74 (m, 1H), 8.53 (d, 1H, J=8.0 Hz), 7.93 (dd, 1H, J=6.4, 3.6 Hz), 7.58–7.63 (m, 4H), 7.29 (d, 2H, J=8.0 Hz), 7.19 (d, 2H, J=8.8 Hz ), 4.40 (s, 2H), 3.28–3.50(m, 4H), 3.08–3.24 (m, 4H ), 2.68–2.84 (m, 2H), 2.14–2.50 (m, 2H), 1.05–1.14 (m, 3H), 0.92–1.02 (m, 3H)

Example 10

Preparation of N,N-diethyl-4-[[(1(4-pyridinylmethyl)-4-piperidinylidene](8-quinolinyl) methyl]benzamide (compound 17)

To a room temperature solution of secondary amine (300 mg; 0.75 mmol) in methanol (8 ml) was added 4-pyridinecarboxaldehyde (241 mg; 2.25 mmol), followed by acetic acid (0.5 ml). The mixture was stirred for 30 minutes then sodium cyanoborohydride (142 mg; 2.25 mmol) was added. The reaction mixture was stirred overnight, then sodium hydroxide 2N was added and the mixture extracted with methylene chloride. Combined methylene chloride extracts were dried over anhydrous sodium sulphate, filtered and concentrated under reduced pressure. Reverse phase purification.

(M+1) calculated: 491.28, (M+1) observed: 491.09

Anal.: calculated for ($C_{32}H_{34}N_4O$ X 2.60 $C_2HO_2F_3$ X 1.50 $H_2O$): C:54.88%; H:4.90%; N:6.88%; found: C:54.87%; H:4.90%; N:6.75%

$^1$HNMR (CD$_3$OD): 8.86–896 (m, 1H), 8.62–8.70 (m, 1H), 8.42–8.52 (m, 1H), 7.88–7.98 (m, 1H), 7.50–7.70 (m, 4H), 7.28–7.38 (m, 3H), 7.16–7.26 (m, 3H), 4.36 (s, 2H), 2.90–3.60 (m, 8H), 2.50–2.90 (m, 2H), 2.00–2.40 (m, 2H), 0.82–1.16 (m, 6H)

Pharmaceutical Compositions

The novel compounds according to the present invention may be administered orally, intramuscularly, subcutaneously, topically, intranasally, intraperitoneally, intrathoracially, intravenously, epidurally, intrathecally, intracerebroventricularly and by injection into the joints.

A preferred route of administration is orally, intravenously or intramuscularly.

The dosage will depend on the route of administration, the severity of the disease, age and weight of the patient and other factors normally considered by the attending physician, when determining the individual regimen and dosage level as the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low melting wax, cocoa butter, and the like.

Salts include, but are not limited to pharmaceutically acceptable salts. Examples of pharmaceutically acceptable salts within the scope of the present invention include: acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, isethionate, lactate, lactobionate, malate, maleate, mandelate, mesylate, methylbromide, methynitrate, methylsulfate, mucate, napsylate, nitrate, pamoate (embonate), pantothenate, phosphatetdiphosphate, polygalacturonate, salicylate, stearate, subacetate, succinate, sulfate, tannate, tartrate, teoclate. Examples of pharmaceutically unacceptable salts within the scope of the present invention include: hydroiodide, perchlorate, and tetrafluoroborate. Preferred pharmaceutically acceptable salts are the hydrochlorides, sulfates and bitartrates. The hydrochloride and sulfate salts are particularly preferred.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other. suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Biological Evaluation
In vitro Model
Cell Culture

A. Human 293S cells expressing cloned human $\mu$, $\delta$, and $\kappa$ receptors and neomycin resistance were grown in suspension at 37° C. and 5% $CO_2$ in shaker flasks containing calcium-free DMEM10% FBS, 5% BCS, 0.1% Pluronic F-68, and 600 $\mu$g/ml geneticin.

B. Mouse and rat brains were weighed and rinsed in ice-cold PBS (containing 2.5 mM EDTA, pH 7.4). The brains were homogenized with a polytron for 15 sec (mouse) or 30 sec (rat) in ice-cold lysis buffer (50mM Tris, pH 7.0, 2.5mM EDTA, with phenylmethylsulfonyl fluoride added just prior use to 0.5 MmM from a 0.5 M stock in DMSO:ethanol).

Membrane Preparation

Cells were pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension was spun at 1000 g (max) for 10 min at 4° C. The supernatant was saved on ice and the pellets resuspended and spun as before. The supernatants from both spins were combined and spun at 46,000 g (max) for 30 min. The pellets were resuspended in cold Tris buffer (50 mM Tris/Cl, pH 7.0) and spun again. The final pellets were resuspended in membrane buffer (50 mM Tris, 0.32 sucrose, pH 7.0). Aliquots (1 ml) in polypropylene tubes were frozen in dry ice/ethanol and stored at −70° C. until use. The protein concentrations were determined by a modified Lowry assay with sodium dodecyl sulfate.

Binding Assays

Membranes were thawed at 37° C. cooled on ice, passed 3 times through a 25-gauge needle, and diluted into binding buffer (50 mM Tris, 3 mM $MgCl_2$, 1 mg/ml BSA (Sigma A-7888), pH 7.4, which was stored at 4° C. after filtration through a 0.22 m filter, and to which had been freshly added 5 $\mu$g/ml aprotinin, 10 $\mu$M bestatin, 10 $\mu$M diprotin A, no DTT). Aliquots of 100 $\mu$l were added to iced 12×75 mm polypropylene tubes containing 100 $\mu$l of the appropriate radioligand and 100 $\mu$l of test compound at various concentrations. Total (TB) and nonspecific (NS) binding were determined in the absence and presence of 10 $\mu$M naloxone respectively. The tubes were vortexed and incubated at 25° C. for 60–75 min, after which time the contents are rapidly vacuum-filtered and washed with about 12 ml/tube iced wash buffer (50 mM Tris, pH 7.0, 3 MM $MgCl_2$) through GF/B filters (Whatman) presoaked for at least 2 h in 0.1% polyethyleneimine. The radioactivity (dpm) retained on the filters was measured with a beta counter after soaking the filters for at least 12 h in minivials containing 6–7 ml scintillation fluid. If the assay is set up in 96-place deep well plates, the filtration is over 96place PEI-soaked unifilters, which were washed with 3×1 ml wash buffer, and dried in an oven at 55° C. for 2 h. The filter plates were counted in a TopCount (Packard) after adding 50 $\mu$l MS-20 scintillation fluid/well.

Functional Assays

The agonist activity of the compounds is measured by determining the degree to which the compounds receptor complex activates the binding of GTP to G-proteins to which the receptors are coupled. In the GTP binding assay, GTP $[\gamma]^{35}S$ is combined with test compounds and membranes from HEK-293S cells expressing the cloned human opioid receptors or from homogenised rat and mouse brain. Agonists stimulate $GTP[\gamma]^{35}S$ binding in these membranes. The $EC_{50}$ and $E_{max}$ values of compounds are determined from dose-response curves. Right shifts of the dose response curve by the delta antagonist naltindole are performed to verify that agonist activity is mediated through delta receptors.

Data Analysis

The specific binding (SB) was calculated as TB-NS, and the SB in the presence of various test compounds was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean ±S.E.M. values of $IC_{50}$, $K_i$ and $n_H$ were reported for ligands tested in at least three displacement curves. Biological data are tabulated on the following pages in Table 1.

TABLE 1

Biological data.

| Ex. # | MOLECULAR STRUCTURE | HDELTA | HDELTA EC50 | % EMax | RAT BRAIN EC50 | % EMax | MOUSE BRAIN EC50 | % EMax |
|---|---|---|---|---|---|---|---|---|
| 2 | | 1.08 | 0.49 | 90.48 | 3.88 | 103.53 | 3.6 | 111.62 |
| 3 | | 0.727 | 0.18 | 102.7 | 4.29 | 129.65 | 8.39 | 145.68 |
| 4 | | 0.762 | 0.26 | 98.49 | 1.85 | 120.16 | 3.71 | 140.12 |

TABLE 1-continued

Biological data.

| Ex. # | MOLECULAR STRUCTURE | HDELTA | HDELTA EC50 | % EMax | RAT BRAIN EC50 | % EMax | MOUSE BRAIN EC50 | % EMax |
|---|---|---|---|---|---|---|---|---|
| 5 | 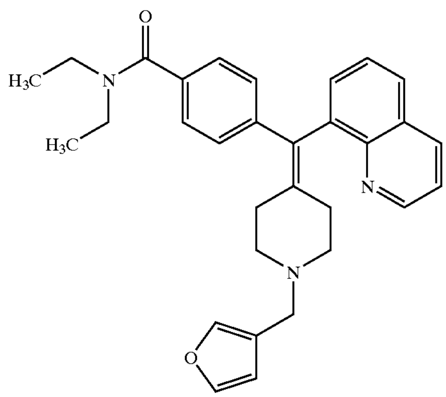 | 0.404 | 0.14 | 99.04 | 1.05 | 135.2 | 2.06 | 146.91 |
| 6 | 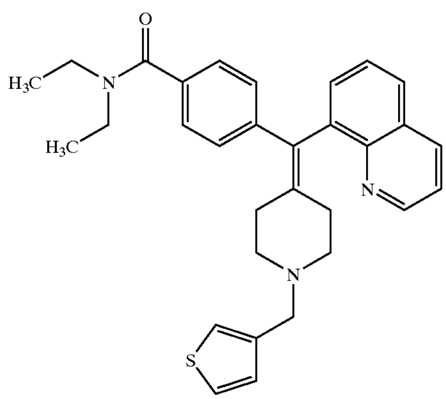 | 0.549 | 0.38 | 122.78 | 3.45 | 134.62 | 4.41 | 140.21 |
| 7 | 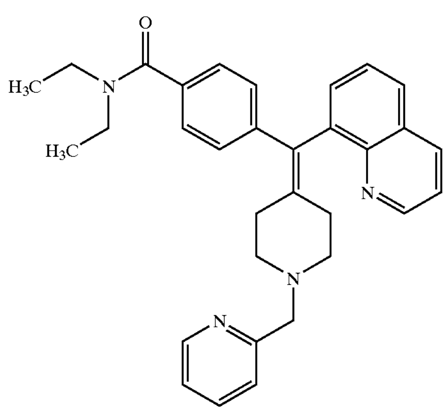 | 0.563 | 0.25 | 97.6 | 2.32 | 126.28 | 2.88 | 124.31 |

TABLE 1-continued

Biological data.

| Ex. # | MOLECULAR STRUCTURE | HDELTA | HDELTA EC50 | % EMax | RAT BRAIN EC50 | % EMax | MOUSE BRAIN EC50 | % EMax |
|---|---|---|---|---|---|---|---|---|
| 8 | (structure: N,N-diethylbenzamide linked to piperidinylidene-quinoline with imidazol-2-ylmethyl on piperidine N) | 0.381 | 0.28 | 110.98 | 3.84 | 148.15 | 4.59 | 138.38 |
| 9 | (structure: N,N-diethylbenzamide linked to piperidinylidene-quinoline with imidazol-4-ylmethyl on piperidine N) | 0.808 | 1.9 | 100.25 | 38.34 | 112.17 | 59.61 | 122.69 |
| 10 | (structure: N,N-diethylbenzamide linked to piperidinylidene-quinoline with pyridin-4-ylmethyl on piperidine N) | 0.765 | 0.8 | 118.41 | 33.5 | 108.52 | 37.8 | 110.11 |

Receptor Saturation Experiments

Radioligand Kδ values were determined by performing the binding assays on cell membranes with the appropriate radioligands at concentrations ranging from 0.2 to 5 times the estimated Kδ (up to 10 times if amounts of radioligand required are feasible). The specific radioligand binding was expressed as pmole/mg membrane protein. Values of Kδ and $B_{max}$ from individual experiments were obtained from non-linear fits of specifically bound (B) vs. nM free (F) radioligand from individual according to a one-site model.

Determination of Mechano-allodynia Using Von Frey Testing

Testing was performed between 08:00 and 16:00 h using the method described by Chaplan et al. (1994). Rats were placed in Plexiglas cages on top of a wire mesh bottom which allowed access to the paw, and were left to habituate for 10–15 min. The area tested was the mid-plantar left hind paw, avoiding the less sensitive foot pads. The paw was touched with a series of 8 Von Frey hairs with logarithmically incremental stiffness (0.41, 0.69, 1.20, 2.04, 3.63, 5.50, 8.51, and 15.14 grams; Stoelting, Ill., USA). The von. Frey hair was applied from underneath the mesh floor perpendicular to the plantar surface with sufficient force to cause a slight buckling against the paw, and held for approximately 6–8 seconds. A positive response was noted if the paw was sharply withdrawn. Flinching immediately upon removal of the hair was also considered a positive response. Ambulation was considered an ambiguous response, and in such cases the stimulus was repeated.

Testing Protocol

The animals were tested on postoperative day 1 for the FCA-treated group. The 50% withdrawal threshold was determined using the up-down method of Dixon (1980). Testing was started with the 2.04 g hair, in the middle of the series. Stimuli were always presented in a consecutive way, whether ascending or descending. In the absence of a paw withdrawal response to the initially selected hair, a stronger stimulus was presented: in the event of paw withdrawal, the next weaker stimulus was chosen. Optimal threshold calculation by this method requires 6 responses in the immediate vicinity of the 50% threshold, and counting of these 6 responses began when the first change in response occurred, e.g. the threshold was first crossed. In cases where thresholds fell outside the range of stimuli, values of 15.14 (normal sensitivity) or 0.41 (maximally allodynic) were respectively assigned. The resulting pattern of positive and negative responses was tabulated using the convention, X=no withdrawal; O=withdrawal, and the 50% withdrawal threshold was interpolated using the formula:

$$50\% \text{ g threshold} = 10^{(Xf + k\delta)}/10{,}000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds were converted to percent of maximum possible effect (% MPE), according to Chaplan et al. 1994. The following equation was used to compute % MPE:

$$\% \ MPE = \frac{\text{Drug treated threshold (g)} - \text{allodynia threshold (g)}}{\text{Control threshold (g)} - \text{allodynia threshold (g)}} \times 100$$

Administration of Test Substance

Rats were injected (subcutaneously, intraperitoneally, intravenously or orally) with a test substance prior to von Frey testing, the time between administration of test compound and the von Frey test varied depending upon the nature of the test compound.

Writhing Test

Acetic acid will bring abdominal contractions when administered intraperitoneally in mice. These will then extend their body in a typical pattern. When analgesic drugs are administered, this described movement is less frequently observed and the drug selected as a potential good candidate.

A complete and typical Writhing reflex is considered only when the following elements are present: the animal is not in movement; the lower back is slightly depressed; the plantar aspect of both paws is observable. In this assay, compounds of the present invention demonstrate significant inhibition of writhing responses after oral dosing of 1–100 μmol/kg.

(i) Solutions Preparation

Acetic acid (AcOH): 120 μL of Acetic Acid is added to 19.88 ml of distilled water in order to obtain a final volume of 20 ml with a final concentration of 0.6% AcOH. The solution is then mixed (vortex) and ready for injection.

Compound (drug): Each compound is prepared and dissolved in the most suitable vehicle according to standard procedures.

(ii) Solutions Administration

The compound (drug) is administered orally, intraperitoneally (i.p.), subcutaneously (s.c.) or intravenously (i.v.)) at 10 ml/kg (considering the average mice body weight) 20, 30 or 40 minutes (according to the class of compound and its characteristics) prior to testing. When the compound is delivered centrally: Intraventricularly (i.c.v.) or intrathecally (i.t.) a volume of 5 μL is administered.

The AcOH is administered intraperitoneally (i.p.) in two sites at 10 ml/kg (considering the average mice body weight) immediately prior to testing.

(iii) Testing

The animal (mouse) is observed for a period of 20 minutes and the number of occasions (Writhing reflex) noted and compiled at the end of the experiment. Mice are kept in individual "shoe box" cages with contact bedding. A total of 4 mice are usually observed at the same time: one control and three doses of drug.

What is claimed is:

1. A compound of the formula I

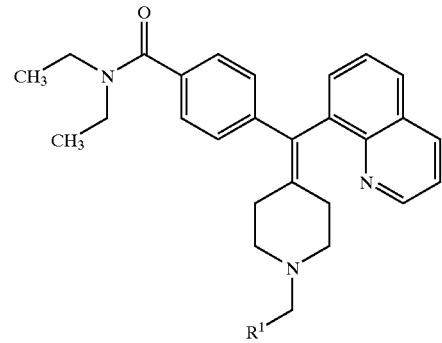

wherein

R$^1$ is selected from any one of

phenyl;

pyridinyl;

thienyl;

furanyl;

imidazolyl;

triazolyl;

where each $R^1$ phenyl ring and $R^1$ heteroaromatic ring may independently be substituted by 1, 2 or 3 substituents selected from: a straight or branched $C_1$–$C_6$ alkyl, $NO_2$, $CF_3$, $C_1$–$C_6$ alkoxy, chloro, fluoro, bromo, and iodo; as well as salts thereof.

2. A compound according to claim 1, wherein said 1, 2 or 3 substituents are selected from the group consisting of: methyl, $CF_3$, chloro, fluoro, bromo, and iodo.

3. A compound according to claim 1, wherein said 1, 2 or 3 substituents are methyl groups.

4. A compound according to claim 1, wherein $R^1$ is pyridinyl, thienyl or furanyl.

5. A compound according to claim 1, selected from any one of

N,N-Diethyl-4-(8-quinolinyl-N-benzyl-piperidin4-ylidene-methyl)-benzamnide;

N,N-diethyl-4-[[1-(2-furylmethyl)-4-piperidinylidene](8-quinoline) methyl]benzamide;

N,N-diethyl-4-{8-quinolinyl[1-(2-thienylmethyl)-4-piperidinylidene]methyl}benzamide;

N,N-diethyl-4-[[1-(3-furylmethyl)-4-piperidinylidene](8quinolinyl)methyl]benzamide;

N,N-diethyl-4-{8-quinolinyl[1-(3-thienylmethyl)-4-piperidinylidene]methyl) }benzamide;

N,N-diethyl-4-[[1-(2-pyridinylmethyl)-4-piperidinylidene](8-quinolinyl) -methyl]benzamide;

N,N-diethyl-4-[[1-(1H-imidazol-2-ylmethyl)-4-piperidinylidene](8-quinolinyl) -methyl]benzamide;

N,N-diethyl-4-[[(1H-imidazol-4-ylmethyl)-4-piperidinylidene](8-quinolinyl) -methyl]benzamide; and N,N-diethyl-4-[[1-(4-pyridinylmethyl)-4-piperidinylidene](8-quinolinyl) -methyl]benzamide.

6. A compound according to any of the preceding claims, in form of its hydrochloride, dihydrochloride, sulfate, tartrate, ditrifluoroacetate or citrate salts.

7. A process for preparing a compound of formula I, comprising:

a) reacting a compound of the general formula II

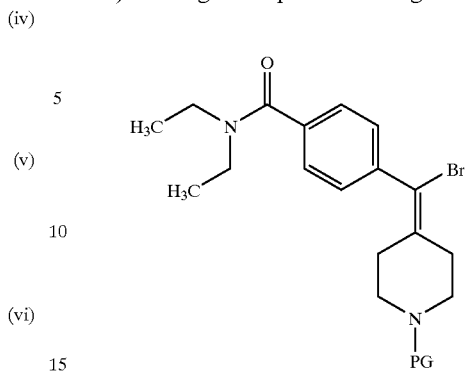

wherein PG is a urethane or benzyl-like protecting group with 8-quinolinyl boronic acid, using a palladium catalyst in the presence of a base to give the compounds of general formula III,

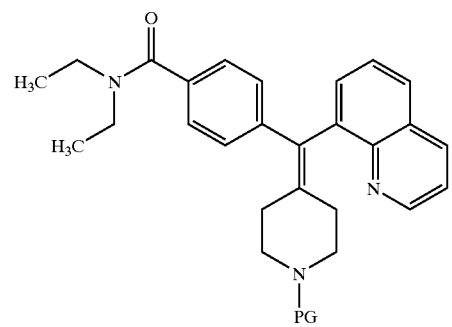

b) deprotecting said compounds of formula III under standard conditions, and c) alkylating the deprotected compounds produced in step b) under reductive conditions with a compound of the general formula $R^1$—CHO to give compounds of the general formula I.

8. A pharmaceutical composition comprising a compound of the formula I according to claim I as an active ingredient, together with a pharmaceutically acceptable carrier.

9. A method for the treatment of pain, whereby an effective amount of a compound of the formula I according to claim 1 is administered to a subject in need of pain management.

10. A method for the treatment of gastrointestinal disorders, whereby an effective amount of a compound of the formula I according to claim 1, is administered to a subject suffering from said gastrointestinal disorder.

11. A method for the treatment of spinal injuries, whereby an effective amount formula I according to claim 1, is administered to a subject suffering from a spinal injury.

* * * * *